(12) United States Patent
Weaver et al.

(10) Patent No.: US 6,641,776 B1
(45) Date of Patent: Nov. 4, 2003

(54) METHOD FOR PREPARING RADIOPAQUE SURGICAL IMPLEMENT

(75) Inventors: Timothy J. Weaver, Duvall, WA (US); Dion Mraz, Mercer Island, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 143 days.

(21) Appl. No.: 09/713,064

(22) Filed: Nov. 15, 2000

(51) Int. Cl.⁷ .......................... C22C 32/00; B28B 1/24
(52) U.S. Cl. ................ 264/642; 264/645; 264/656; 419/10; 419/12; 419/13; 419/14; 419/19
(58) Field of Search ................ 264/642, 645, 264/656; 419/10, 12, 13, 14, 19

(56) References Cited

U.S. PATENT DOCUMENTS

| | | | |
|---|---|---|---|
| 4,321,042 A | 3/1982 | Scheicher | 433/201 |
| 4,927,866 A | 5/1990 | Purrmann et al. | 523/115 |
| 5,062,798 A | 11/1991 | Tsuge et al. | 433/201.1 |
| 5,344,456 A | 9/1994 | Nonami et al. | 623/16 |
| 5,490,962 A | 2/1996 | Cima et al. | 264/22 |
| 5,503,771 A * | 4/1996 | Staley et al. | 252/313.1 |
| 5,679,470 A | 10/1997 | Mayer | 428/662 |
| 5,725,570 A | 3/1998 | Heath | 623/1 |
| 5,733,326 A | 3/1998 | Tomonto et al. | 623/1 |
| 5,972,027 A | 10/1999 | Johnson | 623/1 |
| 5,989,476 A * | 11/1999 | Lockard et al. | 264/401 |
| 6,017,338 A | 1/2000 | Brucker et al. | 606/41 |
| 6,027,528 A | 2/2000 | Tomonto et al. | 623/1 |
| 6,080,808 A | 6/2000 | Sterzel | 524/430 |
| 6,087,024 A | 7/2000 | Whinnery et al. | 428/613 |

FOREIGN PATENT DOCUMENTS

| | | |
|---|---|---|
| EP | 0 444 475 | 2/1991 |
| EP | 0 446 708 | 2/1991 |
| EP | 0423509 | 4/1991 |
| EP | 0462512 | 12/1991 |
| WO | 99 54075 | 10/1999 |

* cited by examiner

*Primary Examiner*—Christopher A. Fiorilla
(74) *Attorney, Agent, or Firm*—Vidas, Arrett & Steinkraus

(57) ABSTRACT

X-ray imageable articles, for instance surgical implements or parts therefore which are used in minimally invasive surgical procedures, may be prepared by a process including the steps of:

(a) preparing a mixture composition comprising:
   i) radiolucent particulate material selected from ceramic materials, metallurgic materials, and combinations thereof and having a particulate size of no more than 40 microns,
   ii) radiopaque particulate material selected from ceramic materials, metallurgic materials, and combinations thereof and having a particulate size of no more than 40 microns, and
   iii) at least one polymeric binder material;
(b) injection molding the mixture composition into a preform;
(c) optionally removing the binder material from the preform; and (d) sintering the preform.

10 Claims, 1 Drawing Sheet

10

20

30

METHOD FOR PREPARING RADIOPAQUE SURGICAL IMPLEMENT

BACKGROUND OF THE INVENTION

This invention relates to medical devices which are inserted into the body and located by X-ray imaging.

Various types of minimally invasive surgical techniques have been developed in recent years in which catheters or similar devices are used to convey a operative implement through a body passage, including such passages as the blood vessels, gastrointestinal tract, urethral and urethral tracts, bronchial and esophageal tracts, to a specific location where the implement is operatively employed or delivered. Catheters are used to perform balloon angioplasty, to deliver and lodge stent devices, to deliver drugs, to abrade or volatilize lesions, to remove temporary, misplaced or dislodged stents, and the like. For such activities, X-ray imaging is often used to follow the catheter or the operative implement as it traverses the body channel and/or to monitor the actual employment or deployment of the implement.

For materials which are transparent to X-ray, or are only weakly radiopaque, it has been conventional to provide radiopaque marker bands, coatings or laminates of more intensely radiopaque materials on the devices or implements in order to achieve the necessary contrast for a readily observable image.

A number of the implements, used or delivered by such techniques, or parts thereof may be made of metal or ceramic materials. Traditionally such implements are, or are made up of, small complex machined parts. Stents are an example of such an implement which is typically made by machining metal.

A technique which is known for manufacturing metal and ceramic parts utilizes injection molding and sintering of composite formulations. This technique, designated "CIM" for ceramic articles and "MIM" for metal articles utilizes formulations which are mixtures of a resinous binder material and a very fine powder of the respective ceramic or metal material, which is injection molded to produce a desired shaped article, the molded article typically being somewhat larger than the desired size. The binder is then typically removed by extraction, heating, or both, leaving a shaped structure of the powder material. This structure is sintered to form the final article, typically shrinking by a reproducible amount.

Similar products can be prepared from combining ceramic materials with metallurgic materials to form what is known as a "cermet."

A porous stent formed by a powdered metal sintering process is disclosed in U.S. Pat. No. 5972027, incorporated herein by reference in its entirety. A perfusion tip for an ablation catheter is described in U.S. Pat. No. 6017338, incorporated herein by reference in its entirety.

SUMMARY OF THE INVENTION

The present invention is directed to articles which can be made using a CIM or MIM process, preferably articles which are, or are part, of surgical implement structures such as catheters, forceps, stents, perfusion heads, electrodes, and the like used in minimally invasive surgical procedures and. The invention also relates to CIM or MIM processes for preparing such implements, or parts thereof, in which the ceramic or metal powder material used to form the article comprises a radiolucent material and a radiopaque material.

In a first aspect of the present invention there is provided a method for preparing an X-ray imageable article comprising:
(a) preparing a mixture composition comprising:
   i) radiolucent particulate material selected from ceramic materials, metallurgic materials, and combinations thereof and having an average particulate size of no more than 40 microns,
   ii) radiopaque particulate material selected from ceramic materials, metallurgic materials, and combinations thereof and having an average particulate size of no more than 40 microns, and
   (iii) at least one polymeric binder material;
(b) injection molding the mixture composition into a preform;
(c) optionally removing the binder material from the preform; and
(d) sintering the preform.

Articles, especially surgical implements comprising an article composed of a sintered mixture of radiolucent and radiopaque powders as described herein, and medical devices comprising such implements are other aspects of the invention.

A further aspect of the invention is a surgical method in which a surgical implement as described herein is carried via a catheter to a remote site within the body and used in performing a surgical procedure, wherein the article of the invention is observed fluoroscopically during at least a portion of the time it is in the body.

Still further aspects of the invention are described in the detailed description below and in the claims.

DETAILED DESCRIPTION

Figure 1:
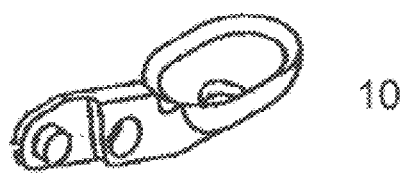
FIG. 1 is a perspective view of a single jaw of a biopsy forceps fashioned in accordance with the present invention.

As noted above the invention is preferably practiced to prepare articles which are, or are components of surgical implements adapted for delivery and operation at a remote site within the body on a catheter.

According to the invention the subject article is composed of a mixture of at least two inorganic ceramic or metallurgic materials, one of which is radiolucent, (i.e. invisible or only weakly visible fluoroscopically), and the second of which is radiopaque (readily visible fluoroscopically).

Particulate materials suitable for the radiolucent inorganic material making up the component (i) of the moldable compositions include:

ceramic materials such as alumina, aluminum nitride, silica, silicon, silicon carbide, silicon nitride, sialon, zirconia, zirconium nitride, zirconium carbide, zirconium boride, titania, titanium nitride, titanium carbide, barium titanate, titanium boride, boron nitride, boron carbide, magnesium oxide, calcium oxide, and the like, and combinations thereof; and metallurigic materials including metals, and mixtures or alloys thereof such as stainless steel, iron, nickel, titanium, nitinol, and metallic oxides which can be converted to metals when sintered in a reducing environment, and combinations thereof.

Combinations of such inorganic radiolucent ceramic and metallurgic materials may also be employed as the component (i). Preferred radiolucent materials include alumina, zirconia, and 17-4 PH, MP35N, 316 LVM, and 304V stainless steels.

Particulate materials suitable for the inorganic radiopaque material making up the component (ii) of the moldable compositions include:

ceramic materials such as tungsten carbide, and tungsten boride, and metallurgic materials such as platinum, tantalum, iridium, tungsten, rhenium gold and alloys of such metals.

Combinations of such inorganic radiopaque ceramic and metallurgic materials may also be employed as the component (ii). Preferred radiopaque materials include platinium, tungsten, rhenium and tantalum.

The morphology of the inorganic particulate materials (i) and (ii) is not critical but is preferably approximately spherical. The particle sizes of the materials will both be within the range suitable for forming sintered articles, suitably an average of about 40 micrometers (microns) or less, more preferably an average of from about 0.5 to about 10 micrometers in diameter.

The ratio of the radiolucent and radiopaque materials may vary widely, depending on the desired structural properties and radiopacity of the finished article. Generally the radiopaque material (ii) will constitute at least 2% and no more than about 75% by volume of the total volume of the components (i) and (ii). More typically, structural and/or cost factors will favor the radiolucent component, so that the radiopaque component will constitute no more than 50% by volume and preferably no more than about 35% by volume of the two. On the other hand, if too little of the radiopaque component is employed the fluoroscopic visibility of the implement may not be adequately enhanced. Consequently it will generally be desirable to employ at least 5% and often 10% or more of the radiopaque component, based on the total volume of these two components.

Also, it is generally preferred that the radiopaque material have a melting point which is not substantially lower than the radiolucent material so that fluidization of the radiopaque material does not occur before the radiolucent material reaches sintering temperature. More preferably the radiopaque material has a melting point which is about the same or is even higher than that of the radiolucent material.

The third component of the composition is a binder material (iii). Any material suitable as a binder material for CIM or EM processes may be used. Exemplary materials include polyolefins, such as polyethylene and propylene; olefin copolymers such as ethylene vinyl acetate copolymers; poly(meth)acrylates including polymethyl methacrylate, polybutyl methacrylate and the like; polystyrene and other styrene group resins; polyvinyl chloride; polyamides; polyesters; polyethers; polyacetals; various types of wax, including paraffin; and the like. Exemplary binders are described in, EP-A-0 446 708 and EP-A-0 444 475, incorporated herein by reference.

The binding agents are employed in conventional amounts, generally from about 2% to about 30% by weight of the injection moldable composition. More preferably the binder will be employed in an amount of from about 4 to about 15% by weight of the composition. Generally lower amounts of binder will be preferred to minimize shrinkage during sintering. However, with very complex shapes, if the shrinkage is carefully controlled to give good reproducibility and avoid shape distortion, high shrinkage may be advantage in allowing larger molds to be used to produce the preform.

In addition to the three components described above, various additives known in the art may be added in conventional to the moldable composition. Examples of such additives include plasticizing agents, lubricating agents, antioxidants, degreasing promotion agents, and surfactants.

The composition of the inorganic powders (i) and (ii), the binder (iii) and any other additives are suitably blended in a kneading machine above the melting point of the binder and the kneaded product pelletized before use. Alternatively any other conventional mixing technique may be used and/or the blended mixture may be used without pelletization.

In the second step of the inventive process the composition produced as described above is injection molded into a compacted preform. The dimensions of the mold are set taking into account the shrinkage that will occur from the later sintering step. Typical molding conditions will provide the composition to the mold at a temperature above the melting point of the binder, typically from about 130–200° C. and at injection pressure of from about 30,000 to as high as 200,000 kPa. The mold temperature suitably will be below that of the composition, and below the glass transition temperature of the binder, typically from about 5° C. to about 50° C. Alternatively the mold may be at a higher temperature when the composition is injected and then subsequently cooled. The preform produced in this step is then removed from the mold.

After the preform is removed from the mold a binder extraction process may be performed on the preform. In forming sintered parts it is not always necessary to remove the binder as it may vaporize/decompose during sintering. However, better dimensional stability results are often obtained if the binder is removed before the preform is sintered. Known binder removal methods include solvent extraction, thermal decomposition/vaporization at a temperature below the sintering temperature, and chemical decompositon, for instance decomposition of polyacetal resins by exposure to an acidic gas at elevated temperature. Combinations of such removal methods may also be employed. Suitable conditions for such binder extractions are known in the art.

Next, the preform, either as obtained directly from the mold or after binder extraction is heated under conditions suitable for sintering the inorganic particles of the components (i) and (ii). Typical conditions will be a temperature of from about 400° C. to about 1700° C. for about 10 to about 30 hours, although higher temperatures and longer or shorter times may be suitable for some articles. Typically the sintering step will be conducted in a non-oxidizing atmosphere, for example, in argon gas or other inactive gases, under a vacuum or reduced pressure conditions. In some instances, for instance where the metallurgic material is a metal oxide, hydrogen will be provided to accomplish a reduction of such oxide to the metal during sintering. A reduction process adaptable to the present invention is described in U.S. Pat No. 6,080,808, incorporated herein by reference.

In some cases surface hardness or other desirable properties may be imparted to the implement by providing an atmosphere containing one or more gas(es) containing least one of C, O or N during a portion of the sintering time. Such gases may be selected from air, $O_2$, $CO_2$, CO, $N_2$, methane, acetylene, propane and mixtures thereof.

After sintering, the formed article may be subjected to any necessary finishing steps. For example, lubricity coatings may be applied, finishing machining may be performed, and/or surface processing may be performed such as shot blasting, honing, grinding, etching, wet plating, vacuum evaporation, ion plating, spattering, CVD, and the like.

The powder injection molding method described above allows complicated shapes to be formed monolithically with a tailored radiopacity in a simple and repeatable high production rate process.

Through adjustment of types of binding agents, added amounts, binder extraction conditions, and sintering conditions, various material properties of the inventive implement can be controlled or set. Examples of such properties include the composition of the surface layer, the pore diameter, and the number of pores.

The invention permits the radiographic contrast range of the article to be tailored to permit ready visualization, without creating an X-ray artifact which masks the surrounding vessel and tissue. This is especially important in surgical techniques practiced via catheters, since, once the article has been delivered to the site of treatment it is often necessary to visualize surrounding tissue in order to successfully perform a procedure. Still further, in the case of an implement, such as a stent, which is left in the body as a result of the procedure, it is important to monitor the tissue condition through the stent subsequent to placement to verify vessel patentcy. For this reason, the implement needs to be bright enough during X-ray fluoroscopy to be seen using an X-ray intensity which allows visualization of the surrounding tissue, but dim enough to be seen through.

Referring now to the Figures, there is shown in FIG. 1 a single jaw 10 of a two-jaw biopsy forceps which may be mounted on a catheter and transported via the vascular system from a remote location to a diseased or transplanted heart and at that location deployed and operated to grab a tissue sample. The forceps is then removed from the body and the tissue sample retrieved for inspection. Such forceps jaws (T-Rex®) are now conventionally made by machining a blank of a medical grade stainless steel. When made in accordance with the present invention from a mixture of powders of a medical grade stainless steel and a radiopaque metal such as platinum or tungsten, the delivery and removal of the forceps, as well as its operation at the heart site, may be more easily monitored than if the forceps jaws are made only from machined stainless steel.

Figure 2:
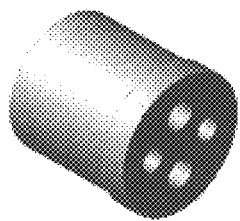
FIG. 2 is an orthagonal view of a ceramic tip for an RF-PMR catheter fashioned in accordance with the present invention.

FIG. 2 shows a perspective view of a ceramic tip 20 for a PMR catheter, conventionally made of alumina by a CIM process. The tip serves an an insulator and mechanical stop for an RF electrode array used to treat myocardial infarction. When made in accordance with the present invention from a mixture of powders of a medical grade alumina and tungsten or rhenium, the delivery and removal of the catheter may be easily monitored without the necessity of providing radiopaque marker bands or the like. Thus the manufacturing process is simplified and components presenting potential bonding issues are eliminated.

Figure 3:
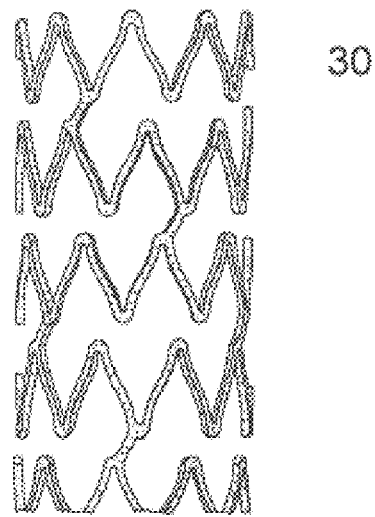
FIG. 3 is a perspective fragmentary view of a stent fashioned in accordance with the present invention.

FIG. 3 shows a porous drug delivery stent 30 of the type described in U.S. Pat. No. 5972027, made from sintered stainless steel powder. When made in accordance with the present invention from a mixture of powders of a medical grade stainless steel and a radiopaque metal such as tantalum, platinum or tungsten, the delivery of the stent, and its functioning to maintain vessel patency may be more easily monitored than if the stent is made only from sintered stainless steel powder.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. Further, the particular features presented in the dependent claims below can be combined with each other in other manners within the scope of the invention such that the invention should be recognized as also specifically directed to other embodiments having any other possible combination of the features of the dependent claims.

What is claimed is:

1. A method for preparing an X-ray imageable surgical implement or component thereof, comprising:

(a) preparing a mixture composition comprising:
  i) radiolucent particulate material selected from ceramic materials, metallurgic materials, and combinations thereof and having an average particulate size of no more than 40 microns,
  ii) radiopaque particulate material selected from ceramic materials, metallurgic materials, and combinations thereof and having an average particulate size of no more than 40 microns, and
  (iii) at least one polymeric binder material;

(b) injection molding the mixture composition into a preform;

(c) optionally removing the binder material from the preform; and (d) sintering the preform.

2. A method as in claim 1 wherein said implement is adapted to be disposed on a catheter and conveyed thereon a remote site within the body and operated at such site to perform a surgical procedure.

3. A method as in claim 2 wherein the radiolucent and the radiopaque powder materials are present in relative amounts which renders the article, when in the body, bright enough during X-ray fluoroscopy to be seen using an X-ray intensity which allows visualization of the surrounding tissue, but dim enough to be seen through.

4. A method as in claim 1 wherein said radiolucent material is selected from the group consisting of alumina, aluminum nitride, silica, silicon, silicon carbide, silicon nitride, sialon, zirconia, zirconium nitride, zirconium carbide, zirconium boride, titania, titanium nitride, titanium carbide, barium titanate, titanium boride, boron nitride, boron carbide, magnesium oxide, calcium oxide, stainless steel, iron, nickel, titanium, nitinol, and metallic oxides which can be converted to metals when sintered in a reducing environment, and combinations thereof.

5. A method as in claim 1 wherein said radiopaque material is selected from the group consisting of tungsten carbide, tungsten boride, the metals platinum, tantalum, iridium, tungsten, rhenium and gold, alloys of said metals, and combinations thereof.

6. A method as in claim 1 wherein the radiopaque material (ii) constitutes at least 2% and no more than about 75% by volume of the total volume of the components (i) and (ii).

7. A method as in claim 1 wherein the radiolucent material is selected from the group consisting of alumina, zirconia and stainless steel and the radiopaque material is selected from the group consisting of platinum, tungsten, rhenium and tantalum, and the radiopaque material constitutes from about 10 to about 50% by volume of the total volume of the components (i) and (ii).

8. A method as in claim 1 wherein the binder component (iii) is selected from the group consisting of polyolefin; olefin copolymers, poly(meth)acrylates; styrene group resins; polyvinyl chloride; polyamides; polyesters; polyethers; polyacetals; and waxes.

9. A method as in claim 1 wherein the binder component (iii) is employed in said mixture composition in an amount of from about 2% to about 30% by weight thereof.

10. A method as in claim 1 wherein the binder removal step c) is performed.

* * * * *